United States Patent
Hindelang et al.

(10) Patent No.: US 10,759,666 B2
(45) Date of Patent: Sep. 1, 2020

(54) HYDROPHOBIC AEROGELS COMPRISING LOW OCCUPANCY OF MONOFUNCTIONAL UNITS

(71) Applicant: Wacker Chemie AG, Munich (DE)

(72) Inventors: Konrad Hindelang, Munich (DE); Dominik Jantke, Eching (DE); Richard Weidner, Burghausen (DE)

(73) Assignee: Wacker Chemie AG, Munich (DE)

( * ) Notice: Subject to any disclaimer, the term of this patent is extended or adjusted under 35 U.S.C. 154(b) by 247 days.

(21) Appl. No.: 15/564,334

(22) PCT Filed: Apr. 21, 2016

(86) PCT No.: PCT/EP2016/058834
§ 371 (c)(1),
(2) Date: Oct. 4, 2017

(87) PCT Pub. No.: WO2016/173912
PCT Pub. Date: Nov. 3, 2016

(65) Prior Publication Data
US 2018/0141821 A1    May 24, 2018

(30) Foreign Application Priority Data
Apr. 29, 2015    (DE) .................. 10 2015 207 945

(51) Int. Cl.
*C01B 33/14*    (2006.01)
*C01B 33/158*    (2006.01)
(Continued)

(52) U.S. Cl.
CPC ....... *C01B 33/1585* (2013.01); *B01J 13/0091* (2013.01); *C01B 33/152* (2013.01);
(Continued)

(58) Field of Classification Search
CPC . B01J 13/0091; B01J 35/0013; C01B 33/152; C01B 33/1546; C01B 33/155; C01B 33/1585
See application file for complete search history.

(56) References Cited

U.S. PATENT DOCUMENTS 4,954,327 A  *  9/1990  Blount ................ C01B 33/1585
                                            106/18.12
5,789,495 A  *  8/1998  Burns .................... C01B 33/16
                                            525/477
(Continued)

FOREIGN PATENT DOCUMENTS

DE        19648798 A1    6/1998
EP        0948395 B1     1/2006
(Continued)

OTHER PUBLICATIONS

English-language Abstract of JP 2003212999 A (2003).
(Continued)

Primary Examiner — Michael A Salvitti
(74) Attorney, Agent, or Firm — Caesar Rivise, PC

(57) ABSTRACT

The problem addressed by the invention is that of producing aerogels which have as high and permanent a hydrophobicity as possible and which have a reduced combustibility, that is as low a carbon content as possible, and are simultaneously less rigid and brittle than known systems, i.e. which with reduced combustibility have a high flexibility and high stability at the same time, that is high mechanical load-bearing capacity. Said problem is solved in that the invention provides gels chosen from lyogel or aerogel, which are synthesised from oxide units and $[R_xSiO_{(4-x)/2}]$ units, wherein the primary particles have a change of concentration in $[R_xSiO_{(4-x)/2}]$ units from the inside to the outside, wherein x can be the same or different and is 1 or 2, and R can be the same or different and is hydrogen or an organic (Continued)

substituted or unsubstituted radical, and wherein the oxide units contain [$SiO_{4/2}$] units, and a method for producing same. The gels provided can be used in cosmetic, medical or for chromatographic applications, and as a catalyst or catalyst support. If the gels are aerogels, same are preferably used for thermal and/or acoustic insulation.

27 Claims, 2 Drawing Sheets

(51) Int. Cl.
*C01B 33/155* (2006.01)
*C01B 33/152* (2006.01)
*B01J 13/00* (2006.01)
*C01B 33/154* (2006.01)
*B01J 35/00* (2006.01)
*E04B 1/74* (2006.01)

(52) U.S. Cl.
CPC ........ *C01B 33/155* (2013.01); *C01B 33/1546* (2013.01); *A61K 2800/60* (2013.01); *B01J 35/0013* (2013.01); *C01P 2006/10* (2013.01); *C01P 2006/12* (2013.01); *E04B 1/74* (2013.01)

(56) References Cited

U.S. PATENT DOCUMENTS

| | | | | |
|---|---|---|---|---|
| 6,129,949 | A * | 10/2000 | Schwertfeger | C01B 33/1585 |
| | | | | 423/338 |
| 6,159,539 | A * | 12/2000 | Schwertfeger | C07F 7/10 |
| | | | | 423/338 |
| 6,378,229 | B1 * | 4/2002 | Hartel | F26B 3/06 |
| | | | | 34/452 |
| 7,470,725 | B2 * | 12/2008 | Schwertfeger | B01J 13/0091 |
| | | | | 106/490 |
| 9,073,759 | B2 * | 7/2015 | Zeng | C01B 33/1585 |
| 9,862,614 | B2 * | 1/2018 | Oh | C01B 33/16 |
| 10,294,111 | B2 * | 5/2019 | Kim | C01B 33/1585 |
| 2001/0034375 | A1 * | 10/2001 | Schwertfeger | B01J 13/0091 |
| | | | | 516/98 |
| 2018/0134565 | A1 * | 5/2018 | Hindelang | C01B 33/152 |
| 2018/0141821 | A1 * | 5/2018 | Hindelang | C01B 33/1585 |

FOREIGN PATENT DOCUMENTS

| | | |
|---|---|---|
| JP | 2003212999 A | 7/2003 |
| KR | 1020110125773 A | 11/2011 |
| WO | 9823366 A1 | 6/1998 |

OTHER PUBLICATIONS

English Abstract for KR 1020110125773 A (2011).
Kanamori et al. (2007). New transparent methylsilsesquioxane aerogels and xerogels with improved mechanical properties. Advanced materials, 19(12), 1589-1593.
Koebel et al. (2011). Aerogels for superinsulation: a synoptic view. In Aerogels Handbook (pp. 607-633). Springer New York.
Rao et al. (2006). Synthesis of flexible silica aerogels using methyltrimethoxysilane (MTMS) precursor. Journal of colloid and interface science, 300(1), 279-285.
Rao et al. (2007). Hydrophobic and physical properties of the ambient pressure dried silica aerogels with sodium silicate precursor using various surface modification agents. Applied surface science, 253(14), 6032-6040.
Yun et al. (2014). Superhydrophobic silica aerogel microspheres from methyltrimethoxysilane: rapid synthesis via ambient pressure drying and excellent absorption properties. RSC Advances, 4(9), 4535-4542.
International Search Report from corresponding PCT/EP2016/058834 dated Jun. 3, 2016.

* cited by examiner

HYDROPHOBIC AEROGELS COMPRISING LOW OCCUPANCY OF MONOFUNCTIONAL UNITS

CROSS-REFERENCE TO RELATED APPLICATIONS

This application is a U.S. National Phase Application of PCT/EP2016/058834, filed Apr. 21, 2016, which claims priority from DE 10 2015 207 945.7, filed Apr. 29, 2015, the contents of which applications are incorporated herein by reference in their entireties for all purposes.

BACKGROUND OF THE INVENTION

The invention relates to gels selected from among lyogel- or aerogel-containing primary particles which are made up of oxidic units and $[R_xSiO_{(4-x)/2}]$ units, wherein the primary particles have a change in the concentration of $[R_xSiO_{(4-x)/2}]$ units from the inside to the outside, where the indices x can be identical or different and are in each case 1 or 2 and the radicals R can be identical or different and are each hydrogen or an organic, substituted or unsubstituted radical, and the oxidic units contain $[SiO_{4/2}]$ units, and also a process for the production thereof.

The invention further relates to the use of the gels of the invention in cosmetic or medical applications, as catalyst or catalyst support, for chromatographic applications, or, when the gels are aerogels, for thermal and/or acoustic insulation.

Thermal insulation to save energy has attained a prominent position in the context of concern for sustainable development and the increasing cost of energy and also ever scarcer fossil raw materials. These requirements for optimization of thermal insulation protection apply equally to buildings, i.e. to new builds or existing buildings, and also to thermal insulation in the logistic or stationary sector.

In the context of durable insulation which has a low thermal conductivity and also a low combustibility, the focus is increasingly on inorganic porous materials.

Aerogels having high porosities (>60%) and a low density (<0.6 g/ml) have a low thermal conductivity and are therefore widely used as thermal insulators (M. A. Aegerter et al. (Eds.), Aerogels Handbook Series: Advances in Sol-Gel Derived Materials and Technologies, 1st ed. 2011, Springer publishers, New York Dordrecht Heidelberg London). Gels, in particular $SiO_2$ gels, are built up of networks which are composed of primary particles which, after linkage and sintering of the contact areas in a sol-gel process, form stable networks filled with liquid, known as lyogels. These lyogels can be converted into aerogels by removal of the solvent. The pores of the aerogel are accordingly filled with air. While the pores are filled with solvent in the case of a lyogel, a hydrogel is a specific case of a lyogel, in which the pore liquid comprises at least 50% of water.

It is desirable to achieve a very high hydrophobicity of $SiO_2$ aerogels in order to reduce the water absorption and as a result the reduction in the thermal insulation effect. Permanent hydrophobicity is achieved by treatment of the surface of gel networks with hydrophobic groups, preferably by modification.

In addition, it is desirable to produce aerogels having a very low combustibility and therefore a very low carbon content (C content).

For further applications in thermal insulation, a very high stability in respect of mechanical influences and flexibility of the thermal insulation materials to be used are also desirable.

Inorganic aerogels, especially those based on $SiO_2$, have been known since 1931 (see, for example, Aegerter et al., Aerogels Handbook 2011, see above). These are produced by formation of a network of $SiO_2$ primary particles by means of a sol-gel process.

EP 0 948 395 B1 describes the production of hydrophobic aerogels based on $SiO_2$. Here, network formation occurs in aqueous solutions to give hydrogels which are subsequently modified by silylation of the accessible Si—OH groups on the surface and are then dried subcritically to give aerogels. The post-silylation leads to a degree of coverage with trimethylsilyl groups (TMS, $(CH_3)_3Si$—) of at least 2.6 $nm^{-2}$, and the C content is accordingly in no case below 6.8% by weight (see table 1).

In addition, these networks have the disadvantages which are generally known in the prior art for aerogels, namely that they are crumbly and brittle (see, for example, introduction of A. V. Rao et al., J. Colloid Interface Sci. 300, 2006, p. 279-285; or Aegerter et al. Aerogels Handbook 2011, see above) since they consist of rigid $SiO_2$ frameworks.

Covering the surface of fully formed $SiO_2$ gel networks (as hydrogel or lyogel) with other silanes, by which means the rigid $SiO_2$ framework is covered with a layer of $[R_xSiO_{(4-x)/2}]$ (where x=1 or 2), is likewise known from the prior art.

However, this construction has the disadvantage that post-modification of the gel network with alkoxysilanes to reinforce the network is associated with multistage and thus complicated solvent replacement steps (A. V. Rao et al., Appl. Surf. Sci. 253, 2007, p. 6032-6040). Since the primary particles are directly joined, i.e. the contact points between the primary particles are in this case, too, formed precisely as described in EP 0 948 395 by rigid $SiO_2$ bridges due to the production method, this process likewise gives brittle products (see FIG. 1). Since the interparticulate linkages are formed before modification, these are made up of $[SiO_{4/2}]$ units (depicted with a light color in FIG. 1).

An alternative approach, namely the direct buildup of aerogels composed of $[CH_3SiO_{3/2}]$ units without subsequent silylation, has been described in the publications by A. V. Rao et al. (2006, see above) and K. Kanamori et al. (Adv. Mater. 19, 2007, p. 1589-1593). Highly flexible aerogels were obtained as products. However, these have a high C content which was calculated as 17.9% by weight despite the omission of subsequent silylation due to the high carbon content of the starting material used. The combustibility of these gels is thus increased compared to the products of EP 0 948 395 (see FIG. 2). The entire gel network and thus also the interparticulate linkages consist of $[R_xSiO_{(4-x)/2}]$ units (depicted in black in FIG. 2). Depending on the starting materials used, the gel therefore has a very high C content.

DESCRIPTION OF THE INVENTION

It is therefore an object of the invention to produce aerogels which have a very high and permanent hydrophobicity and have reduced combustibility, i.e. a very low carbon content, and at the same time display lower rigidity and brittleness than known systems, i.e. possess a high flexibility combined with reduced combustibility.

This object is achieved by the invention which provides gels selected from among lyogel- or aerogel-containing primary particles which are made up of oxidic units and $[R_xSiO_{(4-x)/2}]$ units, wherein the primary particles have a change in the concentration of $[R_xSiO_{(4-x)/2}]$ units from the inside to the outside, where the indices x can be identical or different and are in each case 1 or 2 and the radicals R can be identical or different and are each hydrogen or an organic, substituted or unsubstituted radical, and the oxidic units contain [$SiO_{4/2}$] units.

The gels selected from among lyogels or aerogels preferably contain only primary particles which consist of oxidic units and [$R_xSiO_{(4-x)/2}$] units, wherein the primary particles have a change in the concentration of [$R_xSiO_{(4-x)/2}$] units from the inside to the outside, where the indices x can be identical or different and are in each case 1 or 2 and the radicals R can be identical or different and are each hydrogen or an organic, substituted or unsubstituted radical, and the oxidic units contain [$SiO_{4/2}$] units.

For the purposes of the present invention, a gel is a disperse system which consists of at least two components. The solid component forms a sponge-like, three-dimensional network whose pores are filled by a liquid or a gas. The liquid or gaseous component is thereby immobilized in the solid component. If the pores are filled with solvent, a lyogel is present. If the network is highly porous and air is the incorporated gas, the gel is also referred to as aerogel. According to the invention, the gels are selected from among lyogels or aerogels.

The surface of the gels determined by the BET method in accordance with DIN 9277/66131 and 9277/66132 is preferably in the range from 300 to 1000 m$^2$/g, particularly preferably from 300 to 900 m$^2$/g, particularly preferably from 300 to 800 m$^2$/g.

For the purposes of the invention, primary particles are nanoparticles which, in the sense of a sol-gel process, form the network-forming units of the gel by agglomeration and sintering at the contact areas.

A sol-gel process is, for the purposes of the present invention, a process for producing nonmetallic inorganic or hybrid polymeric materials from colloidal dispersions, known as sols (derived from solution).

For the purposes of the present invention, a sol is a solution and/or colloidal dispersion of molecules and/or particles in at least one solvent or dispersion medium.

A dispersion is a heterogeneous mixture of at least two materials which do not dissolve, or only barely dissolve, in one another or combine chemically with one another. One or more materials (disperse phase) is finely dispersed in another continuous material (dispersion medium, synonym: continuous phase). According to their particle size, dispersed disperse phases having a particle size of typically from about 1 nm to 1 μm are referred to as colloidal.

An agglomeration (lat.: agglomerare—clump together, accumulate) is a more or less solidified accumulation of smaller constituents to form a larger composite.

For the purposes of the present invention, sintering is the strengthening of the contact areas between the individual agglomerated contact areas by incorporation of further monomeric or oligomeric units.

The primary particles of the gels according to the invention are also referred to as optimized primary particles. The gel networks built up of these optimized primary particles are characterized in that they have no direct contacts of purely oxidic particles between the particles, which would lead to very rigid and brittle products. As a result, the gels do not have the disadvantage known from the prior art of direct linkage of primary particles via rigid sinter bridges consisting of pure $SiO_2$. At the same time, the gel networks built up of the optimized primary particles are characterized in that the degree of coverage with monofunctional units and thus the C content is lower. That is to say, the gels of the invention have a high flexibility and at the same time a high stability, i.e. high mechanical strength, combined with reduced combustibility.

According to the invention, the gels contain primary particles which are made up of oxidic units and [$R_xSiO_{(4-x)/2}$] units, wherein the oxidic units contain [$SiO_{4/2}$] units and there is a change in the concentration of [$R_xSiO_{(4-x)/2}$] units in the primary particle from the inside to the outside. Preference is given to at least 75%, particularly preferably at least 90% and in particular at least 99%, of the primary particles present in the gel of the invention being optimized primary particles. In a particularly preferred embodiment, all primary particles present in the gel of the invention are optimized primary particles. In a preferred embodiment, the concentration of [$R_xSiO_{(4-x)/2}$] units goes through a minimum from inside to the outside in the optimized primary particles. The primary particles particularly preferably have an increase in the concentration of [$R_xSiO_{(4-x)/2}$] units from the inside to the outside.

The presence of the elements can be confirmed by determining the elemental composition of a gel by means of elemental analysis.

The presence of various [$R_xSiO_{(4-x)/2}$] units can be checked, and an estimate of the ratios can be made, by means of nuclear magnetic resonance spectroscopy on the solid body, i.e. on the dry gels. Here, the substituent R can be identified by means of $^{13}C$ NMR spectroscopy and the number of substituents x in the [$R_xSiO_{(4-x)/2}$] units where x=0-4 can be determined by means of $^{29}Si$ NMR spectroscopy on the basis of the different chemical shift ranges. The carbon content can be determined using a carbon analyzer, for example from Leco. The coverage of the surface with TMS groups can be calculated from the determination of the BET surface area in accordance with DIN 9277/66131 and 9277/66132 in combination with the results of nuclear magnetic resonance spectroscopy, and this is confirmed by the carbon content.

The calculated degree of coverage with TMS groups can be compared with the appended example for cocondensation, i.e. without a change in the concentration of [$R_xSiO_{(4-x/2)}$] units from the inside to the outside, and also the examples with an increase in the concentration of [$R_xSiO_{(4-x/2)}$] units from the inside to the outside, and a conclusion can be drawn as to the presence of a concentration change. A concentration change in [$R_xSiO_{(4-x/2)}$] units from the inside to the outside is present when the degree of coverage with TMS groups is lower than in the case of cocondensation. The degree of coverage is ideally below 1.5 nm$^{-2}$ after the formation according to the invention.

The formation according to the invention of the primary particles having a concentration change of [$R_xSiO_{(4-x)/2}$] units in the primary particle can, for example, be confirmed by TOF-SIMS (time of flight-secondary ion mass spectrometry), in which different intensities of the observed ion track with increasing ablation of the primary particles can be observed, or by the presence of different contrasts in the center and at the outer periphery of the primary particles by high-resolution TEM methods (transmission electron microscopy).

In the interior, the optimized primary particles thus contain a mixture of [$SiO_{4/2}$] units with other oxidic units, preferably only [$SiO_{4/2}$] units. Since according to the invention the concentration of [$R_xSiO_{(4-x)/2}$] units (where the indices x can be identical or different and are in each case 1 or 2 and the radicals R can be identical or different and R is hydrogen or an organic, substituted or unsubstituted radical) changes, particularly preferably increases from the inside to the outside, either no $[R_xSiO_{(4-x)/2}]$ units at all, or a mixture of oxidic units and $[R_xSiO_{(4-x)/2}]$ units, can be present in the interior of the primary particles in this embodiment.

Since according to the invention the concentration of $[R_xSiO_{(4-y)/2}]$ units (where the indices x can be identical or different and are in each case 1 or 2 and R can be identical or different and R is hydrogen or an organic, substituted or unsubstituted radical) changes, particularly preferably increases from the inside to the outside, the shell or outer husk of the primary particles can contain only $[R_xSiO_{(4-x)/2}]$ units or a mixture of oxidic and $[R_xSiO_{(4-x)/2}]$ units in the particularly preferred structure.

In a particularly preferred embodiment, the concentration increase in $[R_xSiO_{(4-x)/2}]$ units in the primary particles from the inside to the outside is in the form of a gradual, i.e. continuous, not abrupt increase, i.e. in the form of a gradient. This structure will be referred to as gradient structure (see FIG. 3).

The molar proportion of $[R_xSiO_{(4-x)/2}]$ units in the primary particle is preferably below 20 mol %, particularly preferably less than 10 mol % and in particular 0 mol %, in the interior and is increased in the outer direction preferably to more than 80 mol %, particularly preferably increased to more than 90 mol % and in particular increased to 100 mol %.

In a further, particularly preferred embodiment, the primary particles have a structure in the form of a core-shell model, with the core containing a concentration of $[R_xSiO_{(4-x)/2}]$ units of less than 20 mol % and the shell containing a concentration of $[R_xSiO_{(4-x)/2}]$ units of more than 80 mol %. The structure of the primary particles is referred to as core-shell model because the concentration increase in $[R_xSiO_{(4-x)/2}]$ units in the primary particle is present in the form of a sudden increase (for clarification, see FIG. 4). The concentration of $[R_xSiO_{(4-x)/2}]$ units in this case increases from the inside to the outside in the form of an abrupt, sharp concentration step. An abrupt, sharp concentration step means that the molar proportion $[R_xSiO_{(4-x)/2}]$ units in the core is preferably below 20 mol %, particularly preferably below 10 mol % and in particular 0 mol %, and is increased in a concentration step preferably to above 80 mol %, particularly preferably to above 90 mol % and in particular to 100 mol %.

The optimized primary particles of the gels preferably have a layer on the outside composed of $[R_xSiO_{(4-x)/2}]$ units which is sufficient for complete coverage of the particle surface with $[R_xSiO_{(4-x)/2}]$ units. Complete coverage of the particle surface with $[R_xSiO_{(4-x)/2}]$ units means that no $[SiO_{4/2}]$ units are present on the particle surface. The thickness of the layer is selected so that a very small proportion of $[R_xSiO_{(4-x)/2}]$ units is applied. When the primary particles have a structure corresponding to a core-shell model, the layer thickness of the shell of $[R_xSiO_{(4-x)/2}]$ units is preferably less than 3 nm, particularly preferably less than 2 nm and in particular less than 1 nm.

The primary particles of the invention can likewise combine the two concepts. Thus, there can be a gradual increase in the concentration of $[R_xSiO_{(4-x)/2}]$ units in the interior, which is increased in a sharp concentration step in the direction of the outside.

Likewise, the primary particles of the invention can have a structure in which the concentration of $[R_xSiO_{(4-x)/2}]$ units in the primary particle goes through a minimum. Here, it is not relevant whether the minimum is due to a gradual decrease and subsequent increase or due to concentration steps in the proportion of $[R_xSiO_{(4-x)/2}]$ units.

According to the invention, the primary particles of the gels are made up of oxidic units and $[R_xSiO_{(4-x)/2}]$ units, where the oxidic units contain $[SiO_{4/2}]$ units.

The term oxidic units refers to compounds in which a metal atom is bound exclusively to oxygen atoms which in turn each have a free electron for a further bond. As oxidic units, it is possible for $[SiO_{4/2}]$ units with all hydrolysis-stable metal oxides known to those skilled in the art or mixtures thereof to be present; preference is given to trivalent or tetravalent units, particularly preferably only $[SiO_{4/2}]$ units, being present as oxidic units in addition to the $[SiO_{4/2}]$ units.

In the $[R_xSiO_{(4-x)/2}]$ units, where the indices x can be identical or different and are in each case 1 or 2, one or two radicals R are bound directly in addition to one or two oxygen atoms to the silicon atom. It is possible either for one radical R and three oxygen atoms, i.e. x=1, to be bound to the silicon atom in all $[R_xSiO_{(4-x)/2}]$ units, or two radicals R and two oxygen atoms, i.e. x=2, to be bound to the silicon atom in all $[R_xSiO_{(4-x)/2}]$ units. A mixture of $[RSiO_{3/2}]$ units and $[R_2SiO_{2/2}]$ units can also be present. Here too, $O_{(4-x)/2}$ (e.g. $O_{3/2}$, $O_{2/2}$) represents (4-x) (3, 2) oxygen atoms which each have a free electron for a further bond. The above definition applies to R.

The radicals R can be identical or different and are each, independently of one another, hydrogen, an organic, linear, branched, cyclic, saturated or unsaturated, aromatic or heteroaromatic radical, with or without substituents. This means that the radicals R can be substituted or unsubstituted. Preferred substituents are —CN, —NCO, —NR$_2$, —COOH, —COOR, -halogen, -(meth)acryl, -epoxy, —SH, —OH, —CONR$_2$, —O—R, —CO—R, —COO—R, —OCO—R or —OCOO—R, —S—R, —NR—, —N=R, —N=N—R or —P=R. Preference is given to using saturated or unsaturated radicals having from 1 to 4 carbon atoms, particularly preferably $C_1$-$C_4$-alkyl, vinyl, 3-aminopropyl, in particular methyl or ethyl. Special preference is given to R being a methyl group.

On the surface of pure $[SiO_{4/2}]$ gels, each silicon atom has, when the condensable Si—OH groups are fully condensed, at least one free Si—OH group. These free OH groups on the surface of the gels are available for surface modification (silylation), i.e. for reaction with a silylating agent.

The molar proportion of oxidic units in the total gel network made up of the primary particles (i.e. before potential surface modification/silylation of the gels) is preferably more than 1%, particularly preferably above 50%, in particular above 80% and especially preferably above 90%. The molar ratio of the oxidic units to $[R_xSiO_{(4-x)/2}]$ units can be controlled in a simple manner via the amounts of the corresponding starting materials used.

For the purposes of the invention, monofunctional units are M units known from the nomenclature of silicones, i.e. $[R_3SiO_{1/2}]$ units, where the radicals R can be identical or different and the definition given above applies for R. The radicals R are preferably identical, and R is particularly preferably a methyl group. The methyl-based, monofunctional units $[(CH_3)_3SiO_{1/2}]$ unit is thus a trimethylsiloxy unit. Monofunctional units can be introduced by means of silylating agents known to those skilled in the art, for example trimethylchlorosilane, hexamethyldisilazane or hexamethyldisiloxane.

The degree of coverage with TMS groups for $[SiO_{4/2}]$ aerogels which are hydrophobic all through is given in EP 0 948 395 B1 at at least 2.6 nm$^{-2}$, which corresponds to a carbon content of not less than 6.8% by weight.

Gels which are made up all through of $[R_xSiO_{(4-x)/2}]$ units (where x=1 and/or 2) have, on the other hand, no free Si—OH groups on the surface when the condensable Si—OH groups are fully condensed. The C content of the gel is thus determined exclusively by the radical R in the $[R_xSiO_{(4-x)/2}]$ units, and subsequent silylation can no longer occur here in the case of complete condensation.

For this reason, very complete condensation of the condensable free OH groups which are available for silylation is advantageous for a low degree of coverage of monofunctional units. This means that the presence of very few free silylatable OH groups which are available for subsequent silylation is advantageous. The structure according to the invention of the primary particles achieves precisely this: the number of OH groups available for silylation and thus hydrophobicization all through is greatly reduced by the incorporation of Si—R groups (or $[R_xSiO_{(4-x)/2}]$ units where x=1 and/or 2 and the radicals R are identical or different and R is hydrogen or an organic, substituted or unsubstituted radical), so that a reduced degree of coverage compared to a conventional structure of the primary particles is found after silylation.

To achieve a very low C content, it is advantageous for the radicals R of the $[R_xSiO_{(4-x)/2}]$ units (where x=1 and/or 2 and the radicals R are identical or different and R is hydrogen or an organic, substituted or unsubstituted radical) to have very few carbon atoms. It is likewise advantageous for the silylating agent to introduce groups having very few carbon atoms. The number of carbon atoms in the $[R_xSiO_{(4-x)/2}]$ units according to the invention is preferably smaller than the number of carbon atoms in the silylating agent. The groups introduced by means of the modification reaction are particularly preferably TMS groups.

When the monofunctional group introduced is TMS, which during surface modification, introduces three carbon atoms per available, uncondensed OH group, it is particularly advantageous for the $[R_xSiO_{(4-x)/2}]$ units corresponding to the present invention to have 1-2 carbon atoms. Since $(CH_3)_3SiO_{1/2}$ groups (TMS groups) contain 44.4% by weight of carbon, but $[(CH_3)_2SiO_{2/2}]$ units contain only 32.4% by weight of carbon and $[(CH_3)SiO_{3/2}]$ units contain merely 17.8% by weight of carbon, the gels having the structure according to the invention are characterized by a reduced carbon content compared to conventional $[SiO_{4/2}]$ gels saturated with TMS groups. The C content is particularly low when the oxidic core of the gels is very completely enveloped by $[R_xSiO_{(4-x)/2}]$ units, with the molar proportion of $[R_xSiO_{(4-x)/2}]$ units in the total gel network before silylation preferably being not more than 99%, particularly preferably not more than 50%, more preferably not more than 20% and in particular not more than 10%. When the gels are aerogels, the carbon content of the gels of the invention is preferably below 15% by weight, particularly preferably below 10% by weight and in particular below 5% by weight.

The networks according to the invention made up of optimized primary particles preferably have a degree of coverage with monofunctional units, particularly preferably with TMS groups, of less than 1.5 groups per $nm^2$, particularly preferably less than 1.0 group per $nm^2$, in particular less than 0.5 group per $nm^2$ and especially preferably 0.2 group per $nm^2$. In a more preferred embodiment, the gels do not bear any monofunctional units.

As comparative example 1 shows, a gel having a degree of coverage with TMS groups of 2.70 $nm^{-2}$ was produced by classical synthesis of a hydrophobic $SiO_2$ aerogel from water glass after silylation. On the other hand, a pure $[CH_3SiO_{3/2}]$ aerogel (see comparative example 3) had a degree of coverage with TMS groups of 0.22 $nm^{-2}$ after silylation. Comparison of these two experiments clearly shows that a lower proportion of free Si—OH groups, as is the case for $[RSiO_{3/2}]$ gels, results in a significantly lower coverage with TMS groups after silylation.

The buildup of networks from optimized primary particles prevents direct rigid contact due to the production method between $[SiO_{4/2}]$ particles via $[SiO_{4/2}]$ bridges. It is known to those skilled in the art from the literature that networks having contacts composed of $[R_xSiO_{(4-x)/2}]$ units where x=1 and/or 2 give flexible structures (Rao et al. 2006, see above, and K. Kanamori et al. 2007 see above).

The gel networks according to the invention contain the optimized primary particles described. The gels of the invention preferably contain only the optimized primary particles. The connections between the primary particles are stabilized by sintering necks, with these having a high proportion of $[R_xSiO_{(4-x)/2}]$ units comparable to the outer shell of the primary particles and preferably consisting only of
$[R_xSiO_{(4-x)/2}]$ units. The structure according to the invention and linkage of the primary particles via $[R_xSiO_{(4-x)/2}]$ units thus makes flexible aerogels accessible. The combination of flexibility and low carbon content is a substantial, structural advantage of the structures according to the invention.

The lyogels of the invention, in which the pores are filled with a liquid, and the aerogels of the invention, which are obtained after drying from lyogels and whose pores are filled with air, are built up in this way.

When the gels are aerogels, the density of the gel is preferably below 0.25 $g/cm^3$, particularly preferably below 0.15 $g/cm^3$ and in particular below 0.1 $g/cm^3$.

Gels which are aerogels and have a density below 0.15 $g/cm^3$ and have a degree of coverage with monofunctional units of not more than 1 per $nm^2$, a carbon content of not more than 8% by weight and a BET surface area of greater than 300 $m^2/g$ are therefore preferred subject matter of the invention.

Comparative example 2 illustrates the cocondensation of water glass and potassium methylsiliconate, and a degree of coverage with TMS groups of 1.57 $nm^{-2}$ was achieved after silylation. Example 1 according to the invention illustrates the sequential condensation of water glass and potassium methylsiliconate to form a gel according to a gradient model. After silylation, a degree of coverage with TMS groups of 0.71 $nm^{-2}$ was achieved. The significantly lower degree of coverage with TMS groups compared to pure $SiO_2$ gels (comparative example 1) and the noninventive gels from the cocondensation (comparative example 2) demonstrates the increase from the inside to the outside of the concentration of the $[RSiO_{3/2}]$ units. This structure according to the invention led to a significant reduction in the coverage with TMS groups.

Example 2 provides a gel which has a structure in the form of the core-shell model. Colloidal $SiO_2$ particles were used as $[SiO_{4/2}]$ units and these were coated with $[RSiO_{3/2}]$ units from potassium methylsiliconate and joined to form a gel network. A degree of coverage with TMS groups of 0.11 $nm^{-2}$ is achieved after silylation. Example 2 shows that a degree of coverage with TMS groups in the order of that of pure $[RSiO_{3/2}]$ gels (cf. comparative example 3) can be achieved by building up primary particles as core-shell particles and sintering these to form networks. This is at the same time evidence that the cores consisting of pure $SiO_2$ of the particles are completely covered with $[RSiO_{3/2}]$ units and the primary particles are also joined via [RSiO$_{3/2}$] sintering bridges. In the case of uncondensed Si—OH groups being present, as occur on a surface composed of pure SiO$_2$ units, an increased degree of coverage with TMS groups would be found.

The invention further provides a process for producing the gels of the invention by i) placing a sol containing colloidal particles, where the colloidal particles contain oxidic units, in a reaction vessel and ii) reacting the particles in the sol with [R$_x$SiO$_{(4-x)/2}$] units, where the indices x can be identical or different and are in each case 1 or 2 and the radicals R can be identical or different and are each hydrogen or an organic, substituted or unsubstituted radical, and iii) forming a gel from the particles, where the oxidic units contain [SiO$_{4/2}$] units.

According to the invention, a sol containing colloidal particles, where the colloidal particles contain oxidic units and the oxidic units contain [SiO$_{4/2}$] units, is firstly placed in a reaction vessel. This means that a sol containing [SiO$_{4/2}$] units is produced in the 1st step of the process.

For the purposes of the present invention, production of a sol comprises mixing of colloidal particles or starting materials for these with at least one solvent or dispersion medium and optionally further additives. A reaction of the starting materials can also take place during and/or after mixing. Sols derived from alkoxysilanes are, for example, produced by hydrolysis with liberation of the corresponding alcohols. The hydrolysis can be accelerated by adding acid and/or increasing the temperature. Sols derived from water glasses and/or siliconates are, for example, produced by neutralizing the strongly basic alkali metal silicates or alkyl siliconates. This can be effected using methods known to those skilled in the art, e.g. as described in EP 0 948 395 B, by neutralization with mineral acids and by means of acidic ion exchange resins.

As oxidic units, it is possible to use [SiO$_{4/2}$] units with all hydrolysis-stable metal oxides known to those skilled in the art or mixtures thereof; trivalent or tetravalent units are preferably used as oxidic units in addition to the [SiO$_{4/2}$] units, with particular preference being given to using only silicate-containing units.

As starting material for the formation of oxidic units, it is possible to use all condensable metal alkoxides, alkali metal salts, halide salts or further organic or inorganic starting materials known to those skilled in the art. It is likewise possible to use colloidal particles based on the respective metal oxides or mixtures thereof.

As starting material for the formation of [SiO$_{4/2}$] units ([SiO$_{4/2}$] starting material), it is possible to use condensable tetrafunctional or higher-functional silanes, alkoxysilanes, alkyl silicates, alkali metal silicates or colloidal silica particles or solutions known to those skilled in the art. Preference is given to using compounds of the type Si(OR)$_4$, [SiO$_{4/2}$]$_w$[SiO$_{3/2}$ (OR)]$_x$ [SiO$_{2/2}$(OR)$_2$]$_y$ [SiO$_{1/2}$ (OR)$_3$]$_z$ (where w, x, y, z is a nonnegative integer), SiCl$_4$, water glasses or colloidal silica solutions as starting material for [SiO$_{4/2}$] units. The definition given above applies to R.

Particular preference is given to using sodium water glass and/or colloidal silica solution. Special preference is given to using colloidal silica solutions in which the average particle diameter of the silica particles is preferably below 8 nm, particularly preferably below 6 nm, in particular in the range from 1 to 5 nm. The particles preferably have an average diameter in the range from 1 to 8 nm. It is also possible to use mixtures or hydrolysis products of the starting materials mentioned, in particular their hydrolysis products with water and/or alcohols.

The term water glass refers to vitreous, amorphous, water-soluble sodium, potassium and lithium silicates solidified from a melt or aqueous solutions thereof. Neutralization of the salt and hydrolysis form [SiO$_{4/2}$] units from the chain-like Si—O—Si compounds.

According to the invention, the particles in the sol are subsequently reacted with [R$_x$SiO$_{(4-x)/2}$] units. For the purposes of the present invention, reacted/reacting means that the starting materials for the formation of [R$_x$SiO$_{(4-x)/2}$] units are added to the sol with mixing, resulting in a chemical reaction taking place.

As starting material for the formation of [R$_x$SiO$_{(4-x)/2}$] units ([R$_x$SiO$_{(4-x)/2}$] starting material), it is possible to use condensable bifunctional, trifunctional or higher-functional silanes, alkoxysilanes or siliconates known to those skilled in the art. Monofunctional silanes, alkoxysilanes or siliconates can optionally also be used.

Preference is given to using compounds of the type RSi(OR)$_3$, RSiCl$_3$, [RSi(OH)$_{3-n}$(OM)$_n$] (where n is a nonnegative integer, in the range from 0 to 3, and M=Li, Na, K) and hydrolysis and/or condensation products thereof, [[RSiO$_{3/2}$]$_x$ [RSiO$_{2/2}$ (OR)]$_y$ [RSiO$_{1/2}$ (OR)$_2$]$_z$ (where x, y, z are nonnegative integers), R$_2$Si(OR)$_2$, R$_2$SiCl$_2$, [R$_2$Si(OH)$_{2-m}$(OM)$_m$] (where m is a nonnegative integer in the range from 0 to 2 and M=Li, Na, K) and hydrolysis and/or condensation products thereof, [R$_2$SiO$_{2/2}$]$_y$[R$_2$SiO$_{1/2}$ (OR)]$_z$ (where y, z are nonnegative integers), R$_3$SiCl, R$_3$SiOR, R$_3$Si—O—SiR$_3$, R$_3$Si—NH—SiR$_3$, R$_3$SiOH, R$_3$SiOM (where M=Li, Na, K).

Particular preference is given to using methyltrialkoxysilanes, vinyltrialkoxysilanes, dimethyldialkoxysilanes, OH—, OR—, H— or Cl-terminated polydimethylsiloxanes, alkali metal methylsiliconates. The use of methyltriethoxysilane (MTES), methyltrimethoxysilane, potassium methylsiliconate or sodium methylsiliconate as starting material for the [R$_x$SiO$_{(4-x)/2}$] units is especially preferred. It is also possible to use mixtures, hydrolysis products and/or condensation products of the starting materials mentioned, in particular their hydrolysis products with water and/or alcohols.

Preference is given to at least one radical R of the [R$_x$SiO$_{(4-x)/2}$] units being organic in nature, i.e. at least one Si—C bond being present; particular preference is given to at least one radical R being a methyl group, and special preference is given to all radicals R of the [R$_x$SiO$_{(4-x)/2}$] units being methyl groups.

The gels of the invention contain the above-described optimized primary particles. The production of the gels of the invention can therefore also be carried out by simultaneous addition of optimized primary particles and further particles, for example particles based on [SiO$_{4/2}$] units or [R$_x$SiO$_{(4-x)/2}$] units or homogeneous mixtures thereof. The gels of the invention preferably consist only of the optimized primary particles, and it is therefore advantageous not to react mixtures of particles to form gels but instead provide only the optimized primary particles by the process.

The formation of optimized primary particles can be carried out by sequential condensation, i.e. condensation offset over time, of oxidic units and [R$_x$SiO$_{(4-x)/2}$] units.

The formation of the preferred, optimized primary particles having the gradient structure can be achieved by sequential condensation, i.e. condensation offset over time, of oxidic units from which a particle-containing sol having a very low proportion of remaining monomers and/or oligomers is formed and [R$_x$SiO$_{(4-x)/2}$] units from which mainly the shell of the primary particles and the sintering bridges are formed. It is advantageous here for the initially charged starting materials for the core which is low in $[R_xSiO_{(4-x)/2}]$ units to have been largely reacted to form the sol before addition of the starting materials for the $[R_xSiO_{(4-x)/2}]$-rich shell. The addition offset over time of the $[R_xSiO_{(4-x)/2}]$ starting materials results in enrichment in the form of the above-described gradient in an outward direction (see FIG. 3). However, it is also possible to react the starting materials in mixtures or in another order to form the sol, so that the concentration of $[R_xSiO_{(4-x)/2}]$ units can go through a minimum or else a mixture of $[R_xSiO_{(4-x)/2}]$ units and oxidic units is already present in the primary particle.

The formation of the likewise preferred, optimized primary particles according to the core-shell model can be carried out by initial charging of isolated, oxidic nanoparticles in the absence of monomeric or oligomeric units in solution and subsequent addition of $[R_xSiO_{(4-x)/2}]$ starting materials. In this embodiment, it is possible to use, for example, colloidal suspensions of nanoparticles based on mixtures of various metal oxides; preference is given to using $[SiO_{4/2}]$ particles. This method makes it possible to increase the concentration of the $[R_xSiO_{(4-x)/2}]$ units in an outward direction in the form of a core-shell structure in which only oxidic, preferably $[SiO_{4/2}]$ units are present in the interior of the primary particle and only $[R_xSiO_{(4-x)/2}]$ units are present on the outside and at the sinter necks (see FIG. 4).

The term colloidal particles refers to particles or droplets which are finely dispersed in the dispersion medium (solid, gas or liquid). The size of the individual particles is typically in the nanometer or micron range. According to the invention, the colloidal particles contain $[SiO_{4/2}]$ units, either in admixture with other metal oxides or as pure $SiO_2$. The average diameter of the particles is preferably in the range from 1 to 8 nm, particularly preferably in the range from 1 to 6 nm and in particular in the range from 1 to 5 nm.

To produce primary particles according to the invention having a gradient-like structure or a core-shell structure and sols containing colloidally dissolved primary particles having the described structure, an addition offset over time, i.e. later addition, of at least part of the $[R_xSiO_{(4-x)/2}]$ starting materials is carried out. This addition offset over time of at least part of the $[R_xSiO_{(4-x)/2}]$ starting materials to the still liquid sol results in enrichment of the $[R_xSiO_{(4-x)/2}]$ units on the surface of the sol particles and thus a gradient-like or core-shell-like structure of the primary particles.

Here, it is advantageous to convert the initially charged starting materials largely into the sol before addition of the starting materials for $[R_xSiO_{(4-x)/2}]$. A thorough reaction can be achieved by increasing the temperature and/or waiting time. A later addition offset over time of at least one part of the $[R_xSiO_{(4-x)/2}]$ starting materials to the still liquid sol means, for the purposes of the present invention, that incubation with further stirring is carried out for preferably from 5 minutes to 10 hours, particularly preferably from 30 minutes to 5 hours, in particular from 30 minutes to 2 hours, after the addition of the first starting materials before the remaining starting materials for $[R_xSiO_{(4-x)/2}]$ are added. Here, the liquid sol is preferably maintained at a temperature in the range from 5 to 100° C., particularly preferably from 10 to 80° C., in particular from 15 to 40° C. Particular preference is given to using colloidal nanoparticles based on metal oxides containing $[SiO_{4/2}]$ units as oxidic starting material. Preference is given to using pure $[SiO_{4/2}]$ nanoparticles. The use of colloidal nanoparticles is particularly advantageous because this makes it possible to ensure that the oxidic starting materials have already been reacted completely to form a colloidal sol.

A preferred embodiment of the process comprises adding at least 1% by weight, more preferably at least 25% by weight, particularly preferably at least 50% by weight and in particular at least 80% by weight, of the $[R_xSiO_{(4-x)/2}]$ starting materials only later to the already initially charged starting materials in the step of sol production (step i). In a particularly preferred embodiment, the total amount of the $[R_xSiO_{(4-x)/2}]$ starting materials is added only later to the sol. Colloidal nanoparticles are preferably used as colloidal solution.

The proportion of $[R_xSiO_{(4-x)/2}]$ units (based on the sum of the oxidic units and the $[R_xSiO_{(4-x)/2}]$ units) is in the range from 1 to 99 mol %, preferably from 1 to 50 mol %, particularly preferably from 1 to 20 mol % and in particular from 1 to 10 mol %. In general, the solids content, i.e. the content of oxidic units and $[R_xSiO_{(4-x)/2}]$ units, in the sol is in the range from 3 to 30% by weight, preferably from 5 to 20% by weight, particularly preferably from 8 to 15% by weight.

In a particularly preferred embodiment, $[SiO_{4/2}]$ particles and acid are placed in a reaction vessel and reacted with potassium methylsiliconate solution, as a result of which the $[SiO_{4/2}]$ particles are covered with a $[R_xSiO_{(4-x)/2}]$ shell. The alkaline potassium methylsiliconate solution here serves both as starting material for the $[R_xSiO_{(4-x)/2}]$ units and also as base in order to initiate gel formation. However, it is generally possible for all of the above-described starting materials for $[R_xSiO_{(4-x)/2}]$ units to be used. The reaction mixture can optionally be cooled during sol production. Gel formation is carried out by methods known to those skilled in the art, for example increasing the pH and/or increasing the temperature.

In addition, additives such as IR opacifiers known to those skilled in the art can be added to the sol in order to reduce the thermal conductivity. Likewise, coated and/or uncoated fibers can be added to increase the mechanical stability. As fiber materials, it is possible to use inorganic fibers, e.g. glass fibers or mineral fibers, organic fibers, e.g. polyester fibers, aramid fibers, nylon fibers or fibers of vegetable origin, and also mixtures thereof.

A further feature of the process is that a gel is formed from the sol. Gel formation can occur during or after addition of the starting materials for the formation of $[R_xSiO_{(4-x)/2}]$ units to the sol. That is to say, items ii and iii are not necessarily successive steps; iii can also be carried out during ii.

A pH of from 4 to 10, particularly preferably from 5 to 9, in particular from 6 to 8, is preferably set for gel formation. For this purpose, all bases generally known to those skilled in the art, e.g. $NH_4OH$, $NaOH$, $KOH$, $Al(OH)_3$, silicates or siliconates can be used, with preference being given to using $NH_4OH$ (ammonia), water glass or alkali metal methylsiliconate. In a particularly preferred embodiment, potassium methylsiliconate is used as base. An acceleration of the gel formation time can also be achieved by means of a temperature increase. In general, gel formation is carried out at a temperature in the range from 0° C. to the boiling point of the solvent present, preferably in the range from 15 to 80° C. In a preferred embodiment, the sol is converted into a gel in step ii), i.e. during covering with $[R_xSiO_{(4-x)/2}]$ units.

In an alternative preferred embodiment, the sol is converted into a gel in a step subsequent to step ii), i.e. after covering with $[R_xSiO_{(4-x)/2}]$ units.

After gel formation, it is possible to carry out aging, which can likewise be accelerated by known methods such as pH control and heating. For the purposes of the invention, aging means that the gel is incubated at a temperature in the range from 5 to 100° C., preferably from 50 to 80° C. and in particular at 60° C., and a pH of 4-11, preferably 7-10 and in particular 8-9, for a defined period of time (aging time). The aging time is critical for very complete condensation of the condensable OH groups on the surface which are accessible for silylation. This may take a number of days. The aging time is preferably in the range from 30 minutes to 1 week, particularly preferably from 1 hour to 3 days, in particular from 3 to 48 hours. The lyogel formed can be washed with water, polar or nonpolar organic solvents or mixtures thereof before, during or after any aging carried out, e.g. in order to remove electrolytes or to replace the pore liquid. The lyogel can also be loaded with solvents or solutions of active compounds which are advantageous for the further use of the lyogel via solvent exchange steps. This is, for example, relevant for the use of the lyogels in cosmetic applications.

The gel is optionally subsequently surface-modified. A preferred surface modification is silylation. As silylating agents, it is possible to use all silylating agents known to those skilled in the art, e.g. silanes, chlorosilanes, alkoxysilanes, siloxanes, silanols, silazanes and mixtures or hydrolysis or dissociation products of the silylating agents mentioned. Particular preference is given to using silylating agents which lead to the formation of monofunctional units. This means that the gel is, in this preferred embodiment, covered with monofunctional units by surface modification. The definition given above applies to monofunctional units. Preference is given to using compounds of the type $R_3SiCl$, $R_3SiOH$, $R_3SiOR$, $R_3SiH$, $R_3Si$—O—$SiR_3$, $R_3Si$—NH—$SiR_3$, where R is as defined above. Particular preference is given to using trimethylchlorosilane and/or hexamethyldisiloxane. Initiators such as mineral acids, preferably hydrochloric acid, are optionally also added at the beginning of the silylation reaction. The time for the process of surface modification is preferably less than 12 hours, more preferably in the range from 15 minutes to 3 hours, in particular from 15 minutes to 2 hours and especially preferably from 15 to 60 minutes. The reaction is preferably carried out in the range from 50 to 90° C., particularly preferably from 60 to 80° C. Auxiliaries such as phase compatibilizers can optionally also be present during surface modification.

For the purposes of the present patent application, a phase compatibilizer is a polar compound or mixtures of various compounds of this type which has an appreciable solubility both in the water-rich phase and in the organic phase and thus accelerates mass transfer between the two substantially immiscible phases.

Suitable phase compatibilizers are polar organic compounds or mixtures thereof, for example alcohols, in particular of the chemical formula R—OH, where R is as defined above for radicals R (e.g. methanol, ethanol, isopropanol)

ketones, in particular of the chemical formula $R^1R^2C$=O, where $R^1$ and $R^2$ are identical or different and are as defined above for radicals R (e.g. acetone $(CH_3)_2C$=O)

ethers, in particular of the chemical formula $R^1OR^2$, where $R^1$ and $R^2$ are identical or different and are as defined above for radicals R (e.g. diethyl ether, tetrahydrofuran, dimethoxyethane)

esters, in particular of the chemical formula $R^1COOR^2$, where $R^1$ and $R^2$ are identical or different and are as defined above for radicals R (e.g. ethyl acetate), and interface-active substances such as surfactants.

For the purposes of the present invention, interface-active refers to organic compounds which, owing to their structure, become arranged in the interface between two phases in such a way that they reduce the interfacial tension (=surface tension) and thereby make wetting, for example, possible. By reducing the surface tension, they may promote the mixing of two phases through to formation of an emulsion. Depending on their chemical composition and use, interface-active substances are referred to as wetting agents, detergents (surfactants, soaps) or emulsifiers.

The materials generally each contain a hydrophilic ("water-loving") group which strongly attracts water and a lipophilic ("fat-loving") (hydrophobic) hydrocarbon group which only weakly attracts water molecules.

Subsequently, the gel can optionally be washed. Preference is given to the gel produced by the process of the invention being dried. In general, drying can be carried out either in the supercritical range or in the subcritical range. Drying preferably takes place below the critical point, preferably at temperatures of from −30 to 200° C., particularly preferably from 0 to 150° C., and at pressures of preferably from 0.001 to 20 bar, particularly preferably from 0.01 to 5 bar, in particular from 0.01 to 2 bar. Drying can be carried out by radiating, convective and/or contact drying. Drying is preferably carried out until the gel has a residual solvent content of less than 0.1% by weight.

The gels of the invention are preferably used in cosmetic, medical or chromatographic applications or as catalyst or catalyst support. When the gels are aerogels, these are preferably used for applications in thermal and/or acoustic insulation.

When the gels of the invention are aerogels, the gels of the invention are preferably used in use forms of thermal insulation known to those skilled in the art, for instance as component in inorganic plaster and render systems, optionally in combination with suitable organic and/or inorganic binder systems, after further processing in the form of boards which can be used directly as insulating material or can be used as filler for hollow building blocks, or as ready-to-use mats.

When the gels of the invention are aerogels, these can also be used as materials for acoustic insulation, as stationary phases in liquid and gas chromatography, as additives for cosmetic applications, as catalysts or catalyst supports, or as highly effective adsorbents or absorbents or, for instance, in the medical sector as active ingredient supports. The aerogels of the invention, preferably those having functionalized surfaces (e.g. vinyl, epoxy, aminopropyl), can also be used as additive, e.g. for setting the mechanical properties in polymers, in particular rubbers, elastomers.

When the gels of the invention are lyogels, these can be employed, inter alia, in dispersions, emulsions, pastes and other formulations for cosmetic applications, abrasives, cleaners and polishing compositions.

BRIEF DESCRIPTION OF THE DRAWINGS

The figures illustrate the invention by way of example without restricting it.

EXAMPLES

Figure 1:
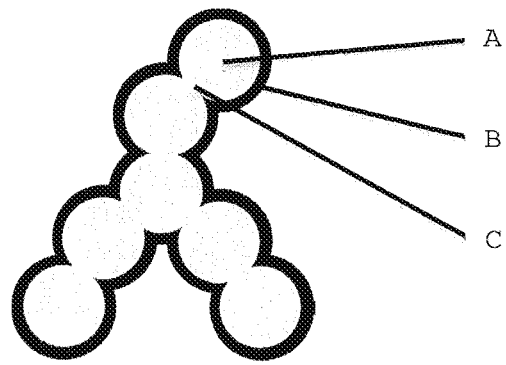
FIG. 1: Schematic depiction of the subsequent modification of existing $[SiO_{4/2}]$ gel networks having interparticular linkages (sintering bridges) composed of $[SiO_{4/2}]$ units (A=core, light-colored center) with $[R_xSiO_{(4-x)/2}]$ units (B=shell, black outer region). Since the interparticular linkages (C) have been formed before the modification, these are shown in light color.
Figure 2:
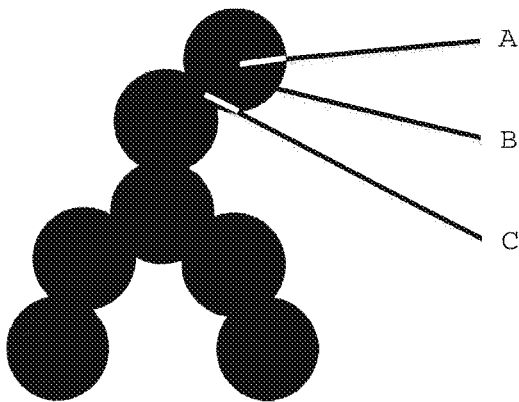
FIG. 2: Schematic depiction of a gel network consisting of $[R_xSiO_{(4-x)/2}]$ units. The entire gel network, i.e. both the core (A), the shell or outer region (B) and the interparticular linkages (C) consist of $[R_xSiO_{(4-x)/2}]$ units.
Figure 3:
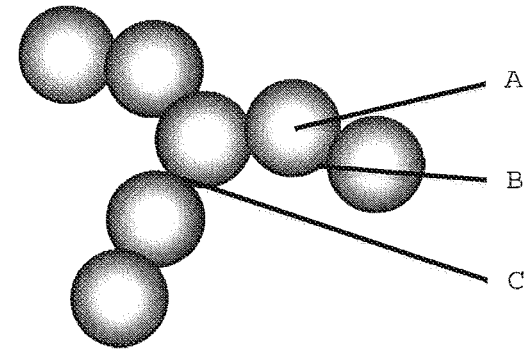
FIG. 3: Schematic depiction of the gradient structure of the primary particles with $[R_xSiO_{(4-x)/2}]$ concentration increasing towards the outside and $[R_xSiO_{(4-x)/2}]$-rich interparticular linkages (sintering bridges, C), where the light-colored center reflects oxidic units with the maximum concentration in the core (A) and the coloration which becomes increasingly dark from the inside to the outside reflects the concentration of $[R_xSiO_{(4-x)/2}]$ units which is low on the inside and increases toward the outside. The sintering bridges (C) have the same composition as the outer shell of the primary particles (B).
Figure 4:
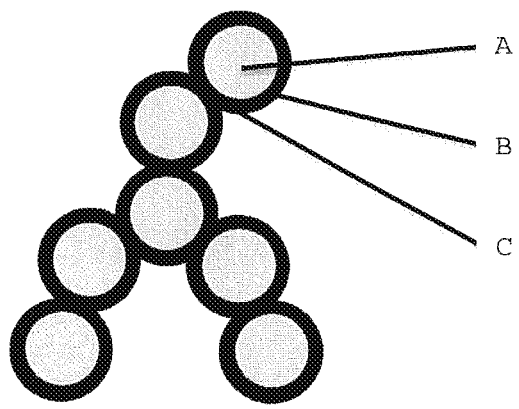
FIG. 4: Schematic depiction of the core-shell structure of the individual primary particles with oxidic core (A, light-colored center) and $[R_xSiO_{(4-x)/2}]$ shell (B, black outer region) and interparticular linkages (C, sintering bridges) of the individual primary particles. Since the sintering bridges have the same composition as the shells, they are shown in black.

The examples illustrate the invention in more detail without restricting its scope.

Analytical Methods:

Determination of the Density

The density of the aerogel pieces was determined by means of pycnometry. For this purpose, the aerogel pieces were weighed on an analytical balance ($m_1$) and to determine the volume the displacement of water was measured in a 25 ml pycnometer (Gay-Lussac glass pycnometer in accordance with DIN ISO 3507 from Blaubrand) at room temperature. For this purpose, the following masses were determined on an analytical balance: $m_2$: mass of the pycnometer filled with distilled water $m_3$: mass of the pycnometer filled with the aerogel pieces and distilled water The volume of the aerogel piece ($V_1$) corresponds to the volume of the displaced water ($V_2$). The volume and the density of the aerogel piece were calculated according to the following formulae:

$$V_1 = V_2 = \rho_w * (m_2 - (m_3 - m_1))$$

$$\rho_{aerogel} = m_1/V_1$$

where $\rho_w$ is the density of water at room temperature (0.998 g/cm³).

When filling the pycnometer with the aerogel piece and the water, care was taken to ensure that no air bubbles were included. Owing to the high hydrophobicity of the aerogel samples, penetration of water into the pores of the samples is ruled out. As a control, the weight of the aerogel pieces was confirmed by renewed weighing after the measurement.

Determination of the BET Surface Area

The specific surface area of the aerogels was determined by the BET method in accordance with DIN 9277/66131 and 9277/66132).

Determination of the Carbon Content

The carbon content (C content) of the samples was determined on a Leco CS 230 analyzer. The analysis was carried out by high-frequency combustion of the sample in a stream of oxygen. Detection was effected by means of nondispersive infrared detectors.

Determination of the pH

The pH was determined using a pH meter from Mettler Toledo, Seven Multi; electrode: In Lab Science.

Calculation of the Degree of Coverage with TMS Groups

The coverage with the TMS groups after surface modification was calculated by means of a method analogous to EP 0 948 395 B1 by means of the following formula:

$$\text{Degree of coverage} = ([C_{with\ TMS}] - [C_{without\ TMS}])/\text{BET}) * K; \text{ unit: } [nm^{-2}]$$

$K = 6.022 * 10^{23}/100 * 12 * 3 * 10^{18} = 167.28$; unit: $[g^{-1}]$ $[C_{with\ TMS}]$: C content after surface modification in % by weight $[C_{without\ TMS}]$: C content before surface modification in % by weight

[BET]: BET surface area; unit: $[m^2/g]$ $$\Delta C[\% \text{ by weight}] = C_{with\ TMS}[\% \text{ by weight}] - C_{without\ TMS}[\% \text{ by weight}]$$

EXAMPLES

Sources:

Water glass (Sigma-Aldrich: $SiO_2$ content: 26.5% by weight, $Na_2O$ content: 10.6% by weight)

Potassium methylsiliconate (SILRES® BS 16 from Wacker Chemie AG: aqueous solution containing 34% by weight of active compound and 20% by weight of $K_2O$)

$SiO_2$ nanosol (Bindzil 17/750 from Akzo Nobel: $SiO_2$ content: 15% by weight, average particle diameter according to manufacturer: 4 nm, pH 10.5)

Hexamethyldisiloxane (AK 0.65 from Wacker Chemie AG)

Trimethylchlorosilane (SILAN M3 from Wacker Chemie AG)

Methyltrimethoxysilane (Sigma-Aldrich, Grade: 98%)

Cetyltrimethylammonium bromide (Sigma-Aldrich)

All further laboratory chemicals were, unless indicated separately, procured from Sigma-Aldrich.

Example 1: Production of an Aerogel from Water Glass and Potassium Methylsiliconate (by Sequential Addition of Potassium Methylsiliconate)

In a glass beaker, 55.5 g of water and 55.5 g of water glass were mixed and cooled to 10° C. in an ice bath. In a second glass beaker, 55.5 g of water and 55.5 g of potassium methylsiliconate were mixed and cooled to 10° C. in an ice bath. 200 g of hydrochloric acid (7.5% by weight) were placed in a screw-cap bottle, cooled to below 10° C. in an ice bath and stirred at 500 rpm by means of a magnetic stirrer.

The cooled water glass solution was added slowly via a dropping funnel to the hydrochloric acid solution while stirring. During the introduction, care was taken to ensure that the dripping rate was so slow that the temperature did not rise above 10° C. After the addition, the reaction mixture was stirred further at room temperature for two hours and cooled back to below 10° C. in an ice bath before addition of the second component. The potassium methylsiliconate solution which had likewise been cooled to below 10° C. in an ice bath was subsequently added slowly via a dropping funnel while stirring, with it being ensured during the introduction that the temperature does not rise above 10° C. The stirring was subsequently stopped and the sol was warmed to room temperature, as a result of which gel formation to form the lyogel took place.

For aging, the lyogel obtained was incubated for 3 hours at 60° C. in a closed vessel in a drying oven. The gel was then pressed through a sieve having a mesh opening of 5 mm in order to obtained pieces smaller than 5 mm.

To remove the salts, the gel pieces were incubated five times for 24 hours in each case in weakly alkaline water having a temperature of 60° C. (300 ml of water per 100 g of gel). Weakly alkaline means that the water was set to a pH of 8.5 using NaOH. The water was separated off by decantation after each 24 hours and subsequently replaced by fresh, weakly alkaline water.

To determine the C content before surface modification, a sample of 10 g of the moist lyogel obtained was dried at 180° C. to constant weight in a drying oven and subsequently analyzed as described above.

In parallel, 100 g of the moist gel obtained before surface modification was covered with 200 ml of an ethanol/water mixture (50% by weight of ethanol) and incubated at room temperature in a closed vessel for 16 hours. The gel was subsequently separated off by filtration on a Büchner funnel (Whatman® Filter, 125 mm, Grade 40). For the surface medication, the gel pieces obtained were admixed with 200 ml of hexamethyldisiloxane and 10.0 g of trimethylchlorosilane in a closed screw-cap bottle, and incubated at 60° C. for 16 hours in a drying oven. The gel pieces were subsequently separated off by filtration on a Büchner funnel (Whatman® Filter, 125 mm, Grade 40) and dried to constant weight under reduced pressure in a vacuum drying oven (10 mbar, 120° C.), giving an aerogel which was subsequently analyzed by the above-described methods.

Particular analytical data of the 1st example:
Density: 0.10 g/cm$^3$
BET: 587 m$^2$/g
C content before surface modification: 9.2% by weight
C content after surface modification: 11.7% by weight
Coverage with TMS groups: 0.71 nm$^{-2}$ Example 2: Production of an Aerogel from Bindzil 17/750 and Potassium Methylsiliconate In a closable glass bottle, 56.6 g of SiO$_2$ nanosol were added while stirring to a solution which was composed of 4.8 g of HCl solution (32% by weight) and 34 g of water and had been cooled to 0° C. 7.6 g of potassium methylsiliconate were subsequently added over a period of 10 minutes while cooling to 0° C., so that a pH of 8 was established. The sample was subsequently warmed to RT, as a result of which gel formation commenced, and this was concluded within 45 minutes. The resulting lyogel, which in this case was a hydrogel, was incubated at 60° C. for 48 hours to effect aging, subsequently broken up in pieces smaller than 5 mm as described in example 1 and the totality of the gel pieces was divided into two parts.

One part (about 50 g) of the gel pieces was, in order to determine the C content before surface modification, washed with water and the solid was dried to constant weight at 120° C. and 10 mbar and subsequently analyzed as described above.

The second part (about 50 g) of the gel pieces was covered with 100 ml of hexamethyldisiloxane. The hydrogel was silylated at 80° C. for 16 hours by addition of 10 g of HCl (32%) and 10 g of ethanol as phase compatibilizer, with the aqueous phase being displaced from the pores. The aqueous phase was separated off and the hydrophobic lyogel obtained was filtered off on a Büchner funnel (Whatman® Filter, 125 mm, Grade 40) and dried to constant weight at 120° C. and 10 mbar, giving an aerogel which was subsequently analyzed using the above-described methods.

Particular analytical data of the 2nd example:
Density: 0.11 g/cm$^3$
BET: 300 m$^2$/g
C content before surface modification: 3.6% by weight
C content after surface modification: 3.8% by weight
Coverage with TMS groups: 0.11 nm$^{-2}$ Comparative Example 1: Gel Formation from Pure SiO$_2$ (method based on EP 0 948 395 B1)
In a glass beaker, 150 g of water and 150 g of water glass were mixed and cooled to 10° C. in an ice bath. 200 g of hydrochloric acid (7.5% by weight) were placed in a screw-cap bottle, cooled to below 10° C. in an ice bath and stirred at 500 rpm by means of a magnetic stirrer.

The cooled water glass solution was slowly added via a dropping funnel to the hydrochloric acid solution while stirring. During the introduction, care was taken to ensure that the temperature does not rise above 10° C. At a pH of 5.2, the addition was stopped and the reaction mixture was warmed to room temperature, as a result of which gel formation took place. To effect aging, the lyogel obtained was incubated at 60° C. for 3 hours in a closed vessel in a drying oven. The gel was then pressed through a sieve having a mesh opening of 5 mm in order to obtain pieces smaller than 5 mm. To remove the salts, the gel pieces were incubated five times for 24 hours each time in weakly alkaline water having a temperature of 60° C. (300 ml of water per 100 g of gel). The water was for this purpose set to a pH of 8.5 using NaOH. The water was separated off by decantation after each 24 hours and subsequently replaced by fresh, weakly alkaline water.

10 g of the moist gel obtained were, to determine the C content before surface modification, dried to constant weight at 180° C. in a drying oven and subsequently analyzed as described above.

100 g of the moist gel obtained were, before surface modification, covered with 200 ml of an ethanol/water mixture (50% by weight of ethanol) and incubated for 16 hours at room temperature in a closed vessel. The gel was subsequently separated off by filtration on a Büchner funnel (Whatman® Filter, 125 mm, Grade 40). To effect the surface modification, the gel pieces obtained were admixed with 200 ml of hexamethyldisiloxane and 10.0 g of trimethylchlorosilane in a closed screw-cap bottle, shaken and incubated at 60° C. for 16 hours in a drying oven. The gel pieces were subsequently separated off by filtration on a Büchner funnel (Whatman® Filter, 125 mm, Grade 40) and dried to constant weight under reduced pressure in a vacuum drying oven (10 mbar, 120° C.), giving an aerogel which was subsequently analyzed using the methods indicated.

Particular analytical data of the 1st comparative example:
Density: 0.20 g/cm$^3$
BET: 521 m$^2$/g
C content before surface modification: <0.1% by weight
C content after surface modification: 8.4% by weight
Coverage with TMS groups: 2.70 nm$^{-2}$ Comparative Example 2: Gel Formation from Water Glass and Potassium Methylsiliconate (by Cocondensation)

In a glass beaker, 150.0 g of water, 75.0 g of water glass and 75.0 g of potassium methylsiliconate were mixed and cooled to 10° C. in an ice bath.

200 g of hydrochloric acid (7.5% by weight) were placed in a screw-cap bottle, cooled to below 10° C. in an ice bath and stirred at 500 rpm by means of a magnetic stirrer.

The cooled water glass-potassium methylsiliconate solution was slowly added to the hydrochloric acid solution via a dropping funnel while stirring. During the introduction, care was taken to ensure that the temperature does not rise above 10° C. At a pH of 5.3, the addition was stopped and the reaction mixture was warmed to room temperature, as a result of which gel formation took place. To effect aging, the gel obtained was incubated for 3 hours at 60° C. in a closed vessel in a drying oven. The gel was then pressed through a sieve having a mesh opening of 5 mm in order to obtain pieces smaller than 5 mm. To remove the salts, the gel pieces were incubated five times for 24 hours each time in weakly alkaline water having a temperature of 60° C. (300 ml of water per 100 g of gel). The water was for this purpose set to a pH of 8.5 using NaOH. The water was separated off by decantation after each 24 hours and subsequently replaced by fresh, weakly alkaline water.

10 g of the moist gel obtained were, to determine the C content before surface modification, dried to constant weight at 180° C. in a drying oven and subsequently analyzed as described above.

100 g of the moist gel obtained were, before surface modification, covered with 200 ml of an ethanol/water mixture (50% by weight of ethanol) and incubated for 16 hours at room temperature in a closed vessel. The gel was subsequently separated off by filtration on a Büchner funnel (Whatman® Filter, 125 mm, Grade 40). To effect the surface modification, the gel pieces obtained were admixed with 200 ml of hexamethyldisiloxane and 10.0 g of trimethylchlorosilane in a closed screw-cap bottle, shaken and incubated at 60° C. for 16 hours in a drying oven. The gel pieces were subsequently separated off by filtration on a Büchner funnel (Whatman® Filter, 125 mm, Grade 40) and dried to constant weight under reduced pressure in a vacuum drying oven (10 mbar, 120° C.), giving an aerogel which was subsequently analyzed using the methods indicated.

Particular analytical data of the 2nd comparative example:
Density: 0.11 g/cm$^3$
BET: 644 m$^2$/g
C content before surface modification: 8.7% by weight
C content after surface modification: 14.8% by weight
Coverage with TMS groups: 1.57 nm$^{-2}$ Comparative Example 3: Gel Formation from [(CH$_3$)SiO$_{3/2}$]

(based on a method of Shan Yun et. al., RSC Adv., 2014, 4, 4535-4542)

315 g of water and 3.0 g of cetyltrimethylammonium bromide (Sigma-Aldrich) were placed in a screw-cap bottle, admixed with 81.8 g of methyltrimethoxysilane while stirring (magnetic stirrer, 500 rpm) and stirred at room temperature for 20 minutes. 3.0 ml of an ammonia solution (1.0 M) were subsequently added while stirring, the mixture was stirred for another one minute and the stirrer was removed, whereupon gel formation commences. To effect aging, the gel obtained was incubated for 16 hours at 60° C. in a closed vessel in a drying oven.

The gel was then pressed through a sieve having a mesh opening of 5 mm in order to obtain pieces smaller than 5 mm. To remove the cetyltrimethylammonium bromide used and the water in the pores, the gel pieces were firstly incubated three times at 50° C. for 24 hours each time in ethanol heated to 50° C. (300 ml of ethanol per 100 g of gel) in a closed vessel. The ethanol was separated off by decantation after each 24 hours and subsequently replaced by fresh ethanol which had been heated to 50° C. The gel pieces were subsequently incubated three times for 24 hours each time in n-hexane which had been heated to 50° C. (300 ml of n-hexane per 100 g of gel) in a closed vessel. The n-hexane was separated off by decantation after each 24 hours and subsequently replaced by fresh n-hexane which had been heated to 50° C. The gel pieces were subsequently separated off by filtration on a Büchner funnel (Whatman® Filter, 125 mm, Grade 40).

10 g of the gel obtained were, in order to determine the C content before surface modification, dried to constant weight under reduced pressure in a vacuum drying oven (10 mbar, 120° C.) and subsequently analyzed as described above.

50.0 g of the gel pieces obtained were, to effect surface modification, admixed with 250 ml of n-hexane and 5.0 g of trimethylchlorosilane in a closed screw-cap bottle, shaken and incubated at 50° C. for 24 hours in a drying oven. The gel pieces were subsequently separated off by filtration on a Büchner funnel (Whatman® Filter, 125 mm, Grade 40), washed twice with 250 ml each time of n-hexane and dried to constant weight under reduced pressure in a vacuum drying oven (10 mbar, 120° C.), giving an aerogel which was subsequently analyzed using the methods indicated.

Particular analytical data of the 3rd comparative example:
Density: 0.25 g/cm$^3$
BET: 615 m$^2$/g
C content before surface modification: 18.0% by weight
C content after surface modification: 18.8% by weight
Coverage with TMS groups: 0.22 nm$^{-2}$ Example 3: Production of an Aerogel from Bindzil 17/750, Methyltriethoxysilane and Dimethyldiethoxysilane In a closable glass bottle, 120 g of SiO$_2$ nanosol were added while stirring to a solution which was composed of 3.2 g of HCl solution (32% by weight) and 22.6 g of water and had been cooled to 0° C., with a pH of 2.5 being established. A mixture of 15.2 g of methyltriethoxysilane and 6.3 g of dimethyldiethoxysilane was subsequently added over a period of 10 minutes while cooling to 0° C. and the mixture was stirred for about 30 minutes. A pH of 8 was subsequently set using an ammonia solution (1 M). The sample was subsequently warmed to RT, as a result of which gel formation commenced and this was concluded within 45 minutes. The resulting lyogel was incubated at 60° C. for 48 hours to effect aging, subsequently broken up into pieces smaller than 5 mm as described in example 1 and the totality of the gel pieces was divided into two parts.

One part (about 50 g) of the gel pieces was, to determine the C content before surface modification, washed with water, the solid was dried to constant weight at 120° C. and 10 mbar and subsequently analyzed as described above.

The second part (about 50 g) of the gel pieces was covered with 100 ml of hexamethyldisiloxane. The hydrogel was silylated at 70° C. for 16 hours by addition of 10 g of HCl (32%) and 10 g of ethanol as phase compatibilizer, with the aqueous phase being displaced from the pores. The aqueous phase was separated off and the hydrophobic lyogel obtained was filtered off on a Büchner funnel (Whatman® Filter, 125 mm, Grade 40) and dried to constant weight at 120° C. and 10 mbar, giving an aerogel which was subsequently analyzed using the above-described methods.

Particular analytical data of the 3rd example:
Density: 0.16 g/cm³
BET: 360 m²/g
C content before surface modification: 7.7% by weight
C content after surface modification: 9.2% by weight
Coverage with TMS groups: 0.69 nm$^{-2}$

TABLE 1

Overview of the particular analytical data of all examples

| Example | Density [g/cm³] | $C_{without\ TMS}$ [% by weight] | $C_{with\ TMS}$ [% by weight] | ΔC [% by weight] | BET [m²/g] | Degree of coverage with TMS groups [nm$^{-2}$] |
|---|---|---|---|---|---|---|
| 1 | 0.10 | 9.2 | 11.7 | 2.5 | 587 | 0.71 |
| 2 | 0.11 | 3.6 | 3.8 | 0.2 | 300 | 0.11 |
| 3 | 0.16 | 7.7 | 9.2 | 1.5 | 360 | 0.69 |
| Comparison 1 | 0.20 | <0.1 | 8.4 | 8.4 | 521 | 2.70 |
| Comparison 2 | 0.11 | 8.7 | 14.8 | 6.1 | 644 | 1.57 |
| Comparison 3 | 0.25 | 18.0 | 18.8 | 0.8 | 615 | 0.22 |

The invention claimed is:

1. A gel comprising lyogel- or aerogel-containing primary particles comprising oxidic units and $[R_xSiO_{(4-x)/2}]$ units, wherein
   the primary particles have an increase in a concentration of $[R_xSiO_{(4-x)/2}]$ units from inside to outside,
   indices x can be identical or different and are in each case 1 or 2,
   radicals R can be identical or different and are each hydrogen or an organic, substituted or unsubstituted radical,
   interparticular linkages of the primary particles comprise $[R_xSiO_{(4-x)/2}]$ units, and
   the oxidic units contain $[SiO_{4/2}]$ units.

2. The gel as claimed in claim 1, wherein the primary particles are built up in a form of a core-shell model, where a core contains a concentration of $[R_xSiO_{(4-x)/2}]$ units of less than 20 mol % and a shell contains a concentration of $[R_xSiO_{(4-x)/2}]$ units of more than 80 mol %.

3. The gel as claimed in claim 1, wherein the radical R is a methyl group.

4. The gel as claimed in claim 1, wherein a degree of coverage with monofunctional units on a surface is less than 1.5 groups per nm².

5. The gel as claimed in claim 1, which is an aerogel having a density of less than 0.25 g/cm³.

6. The gel as claimed in claim 1, which is an aerogel having a carbon content of less than 15% by weight.

7. The gel as claimed in claim 1, which is an aerogel having a density of less than 0.15 g/cm³, a degree of coverage with monofunctional units of not more than 1 per nm², a carbon content of not more than 8% by weight and a BET surface area of greater than 300 m²/g.

8. The gel as claimed in claim 1, wherein only $[SiO_{4/2}]$ units are present as oxidic units.

9. A process for producing gels of claim 1, comprising:
   i) placing a sol containing colloidal particles, where the colloidal particles contain oxidic units, in a reaction vessel, where the oxidic units contain $[SiO_{4/2}]$ units and the sols are produced by neutralization of strongly basic alkali metal silicates or by hydrolysis of alkoxysilanes,
   ii) reacting the particles in the sol with $[R_xSiO_{(4-x)/2}]$ units, where the indices x can be identical or different and are in each case 1 or 2 and the radicals R can be identical or different and are each hydrogen or an organic, substituted or unsubstituted radical,
   iii) and forming a gel from the sol.

10. The process as claimed in claim 9, wherein solutions of colloidal particles containing $[SiO_{4/2}]$ units are used as a starting material, where the particles have an average diameter in a range from 1 to 8 nm.

11. The process as claimed in claim 9, wherein the gel is covered with monofunctional units by surface modification.

12. The process as claimed in claim 9, wherein the gel is dried.

13. The gel as claimed in claim 1, which is an aerogel effective for thermal and/or acoustic insulation.

14. The gel as claimed in claim 1, which is effective for cosmetic, medical or chromatographic applications or as catalysts or catalyst supports.

15. The gel as claimed in claim 1, wherein the primary particles are built up in a form of a core-shell model, where a core contains a concentration of $[R_xSiO_{(4-x)/2}]$ units of less than 20 mol % and a shell contains a concentration of $[R_xSiO_{(4-x)/2}]$ units of more than 80 mol %.

16. The gel as claimed in claim 15, wherein the radical R is a methyl group.

17. The gel as claimed in claim 16, wherein a degree of coverage with monofunctional units on a surface is less than 1.5 groups per nm².

18. The gel as claimed in claim 17, which is an aerogel having a density of less than 0.25 g/cm³.

19. The gel as claimed in claim 18, which is an aerogel having a carbon content of less than 15% by weight.

20. The gel as claimed in claim 19, which is an aerogel having a density of less than 0.15 g/cm³, a degree of coverage with monofunctional units of not more than 1 per nm², a carbon content of not more than 8% by weight and a BET surface area of greater than 300 m²/g.

21. The gel as claimed in claim 20, wherein only $[SiO_{4/2}]$ units are present as oxidic units.

22. A process for producing gels of claim 20, comprising:
   i) placing a sol containing colloidal particles, where the colloidal particles contain oxidic units, in a reaction vessel, where the oxidic units contain $[SiO_{4/2}]$ units and the sols are produced by neutralization of strongly basic alkali metal silicates or by hydrolysis of alkoxysilanes,
   ii) reacting the particles in the sol with $[R_xSiO_{(4-x)/2}]$ units, where the indices x can be identical or different and are in each case 1 or 2 and the radicals R can be identical or different and are each hydrogen or an organic, substituted or unsubstituted radical,
   iii) and forming a gel from the sol.

23. The process as claimed in claim 22, wherein solutions of colloidal particles containing $[SiO_{4/2}]$ units are used as a starting material, where the particles have an average diameter in a range from 1 to 8 nm.

24. The process as claimed in claim 23, wherein the gel is covered with monofunctional units by surface modification.

25. The process as claimed in claim 24, wherein the gel is dried.

26. The gel as claimed in claim 21, which is an aerogel effective for thermal and/or acoustic insulation.

27. The gel as claimed in claim 21, which is effective for cosmetic, medical or chromatographic applications or as catalysts or catalyst supports.

* * * * *